(12) United States Patent
Wachs et al.

(10) Patent No.: US 6,478,238 B1
(45) Date of Patent: Nov. 12, 2002

(54) MINIATURIZED FLUID TRANSFER DEVICE

(75) Inventors: Timothy Wachs, Ithaca, NY (US); Jack D. Henion, Trumansburg, NY (US)

(73) Assignee: Cornell Research Foundation Inc., Ithaca, NY (US)

( * ) Notice: Subject to any disclaimer, the term of this patent is extended or adjusted under 35 U.S.C. 154(b) by 52 days.

(21) Appl. No.: 09/703,902

(22) Filed: Nov. 2, 2000

Related U.S. Application Data

(60) Provisional application No. 60/163,264, filed on Nov. 3, 1999.

(51) Int. Cl.[7] .............................................. A61M 11/06
(52) U.S. Cl. ..................... 239/338; 239/416.4; 239/423
(58) Field of Search ............................... 239/338, 416.4, 239/416.5, 423, 424, 424.5, 426, 429, 434; 128/200.21

(56) References Cited

U.S. PATENT DOCUMENTS

| | | | |
|---|---|---|---|
| 4,746,068 A | 5/1988 | Goodley et al. | 239/405 |
| 4,989,976 A | 2/1991 | Huber | 356/315 |
| 5,464,157 A | 11/1995 | Bourdoulous et al. | 329/424 |
| 5,752,663 A | 5/1998 | Fischer et al. | 239/424 |
| 5,756,994 A | 5/1998 | Bajic | 250/288 |
| 5,856,671 A | 1/1999 | Henion et al. | |
| 5,872,010 A | 2/1999 | Karger et al. | 436/173 |
| 5,884,846 A | 3/1999 | Tan | 239/338 |
| 6,166,379 A | 12/2000 | Montaser et al. | 250/288 |
| 6,175,112 B1 | 1/2001 | Karger et al. | 250/288 |

OTHER PUBLICATIONS

Lee, E.D.; Muck, W.; Henion, J.D.; Covey, T.R., "On–Line Capillary Zone Electrophoresis–Ion Spray Tandem Mass Spectrometry for the Determination of Dinorphins," Journal of Chromatography, 1st ed., Elsevier Science Publishers, B.V. (Amsterdam), pp. 313–321, (Feb. 6, 1988).

Bruins, A.P.; Covey, Thomas R.; & Henion, J.D., "Ion Spray Interface for Combined Liquid Chromatography/Atmospheric Pressure Ionization Mass Spectrometry," Analytical Chemistry, American Chemical Society (USA), vol. 59 (No. 22), pp. 2642–2646, (Feb. 6, 1987).

(List continued on next page.)

Primary Examiner—Lisa A. Douglas
(74) Attorney, Agent, or Firm—Jones, Tullar & Cooper, P.C.

(57) ABSTRACT

A miniaturized ion sprayer device is suitable for coupling with chip-based analytical separation devices, multi-well plates, or surfaces containing residues of prepared samples. One embodiment, a "micro sprayer" device which is suitable for coupling to the terminal edge of a capillary electrophoresis (CE) chip is constructed from modified HPLC tubing and associated fittings and employs a free-standing liquid junction formed via continuous delivery of a flow (1–6 microliters/min) of suitable solvent which carries effluent through a pneumatically-assisted electrospray (ion spray) needle. A second embodiment employs the same features as the microsprayer, but with an extended sampling capillary tube which can reach into the depths of 96, 384, and 1,536 multi-well plates containing either sample solutions or dried sample residues.

20 Claims, 6 Drawing Sheets

OTHER PUBLICATIONS

Jacobson, S.C.; Ramsey, J.M., "Electrokinetic Focusing in Microfabricated Channel Structures," Analytical Chemistry, American Chemical Society (USA), vol. 69 (No. 16), pp. 3212–3217, (Feb. 6, 1997).

Kutter, J.P.; Jacobson, S.C.; Ramsey, J.M., "Integrated Microchip Device with Electrokinetically Controlled Solvent Mixing for Isocratic and Gradient Elution in Micellar Electrokinetic Chromatography," Analytical Chemistry, American Chemical Society (USA), vol. 69 (No. 24), pp. 5165–5171, (Dec. 15, 1997).

Hutt, L.D.; Glavin, D.P.; Bada, J.L.; Mathies, R.A., "Microfabricated Capillary Electrophoresis Amino Acid Chirality Analyzer for Extraterrestrial Exploration," Analytical Chemistry, American Chemical Society (USA), vol. 71 (No. 18), pp. 4000–4006, (Sep. 15, 1999).

Bings, N.H.; Wang, C.; Skinner, C.D.; Colyer, C.L.; Thibault, P.; Harrison, D.J., "Microfluidic Devices Connected to Fused–Silica Capillaries with Minimal Dead Volume," Analytical Chemistry, American Chemical Society (USA), vol. 71 (No. 15), pp. 3292–3296, (Aug. 1, 1998).

Bateman, K.P.; White, R.L.; Thibault, P., "Disposable Emitters for On–Line Capillary Zone Electrophoresis/Nanoelectrospray Mass Spectrometry," Radio Communications in Mass Spectrometry, Crown Copyright, Canada (Canada), pp. 307–315, (Feb. 6, 1997).

Xue, Q.; Dunayevskiy, Y.M.; Frantisek, F.; Karger, B.L., "Integrated Multichannel Microchip Electrospray Ionization Mass Spectrometry: Analysis of Peptides from On–chip Tryptic Digestion of Melittin," Radio Communications in Mass Spectrometry, John Wiley & Sons, Ltd. (Canada), pp. 1253–1256, (Feb. 6, 1997).

Schultz, G.A.; Corso, T.N.; Prosser, S.J.; Zhang, S., "A Fully Integrated Monolithic Microchip Electrospray Device for Mass Spectrometry," Analytical Chemistry, American Chemical Society (Canada), vol. 72 (No. 17), pp. 4058–4063, (Sep. 1, 2000).

Zhang, B.; Liu, H.; Karger, B.L.; Foret, F., "Microfabricated Devices for Capillary Electrophoresis—Electrospray Mass Spectrometry," Analytical Chemistry, American Chemical Soceity (Canada), vol. 71 (No. 15), pp. 3258–3264, (Aug. 1, 1999).

Lazar, I.M., Ramsey, R.S.; Sundberg, S.; and Ramsey, J.M.; "Suattomole–Sensitivity Microchip Nanoelectrospray Source with Time–of Flight Mass Spectrometry Detection," Analytical Chemistry, American Chemical Society (Canada), vol. 71 (No. 17), pp. 3627–3631, (Sep. 1, 1999).

Ramsey, R.S.; Ramsey, J.M., "Generating Electrospray from Microchip Devices Using Electroosmotic Pumping," Analytical Chemistry, American Chemical Society (Canada), vol. 69 (No. 6), pp. 1174–1178, (Mar. 15, 1997).

Figeys, D.; Gygi, S.P.; Mckinnon, G.; Aebersold, R., "An Integrated Microfluidics–Tandem Mass Spectrometry System for Automated Protein Analysis," Analytical Chemistry, American Chemical Society (Canada), vol. 70 (No. 18), pp. 3728–3734, (Sep. 15; 1998).

Figeys, D.; Ning, Y.; Aebersold, R., "A Microfabricated Device for Rapid Protein Identification by Microelectrospray Ion Trap Mass Spectrometry," Analytical Chemistry, American Chemical Society (Canada), vol. 69 (No. 16), pp. 3153–3160, (Aug. 15, 1997).

Xue, Q.; Foret, F.; Dunayevskiy, Y.M.; Zavracky, P.M; McGruer, N.E.; Karger, B.L., "Multichannel Microchip Electrospray Mass Spectrometry," Analytical Chemistry, American Chemical Society (Canada), vol. 69 (No. 3), pp. 426–430, (Feb. 1, 1997).

Jacobson, S.C.; Culbertson, C.T.; Daler, J.E.; Ramsey, J.M., "Microchip Structures for Submillisecond Electrophoresis," Analytical Chemistry, American Chemical Society (Canada), vol. 70 (No. 16), pp. 3476–3480, (Aug. 15, 1998).

Lee, E.D.; Muck, W., Henion, J.D., "Liquid Junction Coupling for Capillary Zone Electrophoresis/Ion Spray Mass Spectrometry," Biomedical & Environmental Mass Spectrometry, John Wiley & Sons, Ltd. (United Kingdom), pp. 844–850, (May 1, 1989).

Detail of Liquid Junction

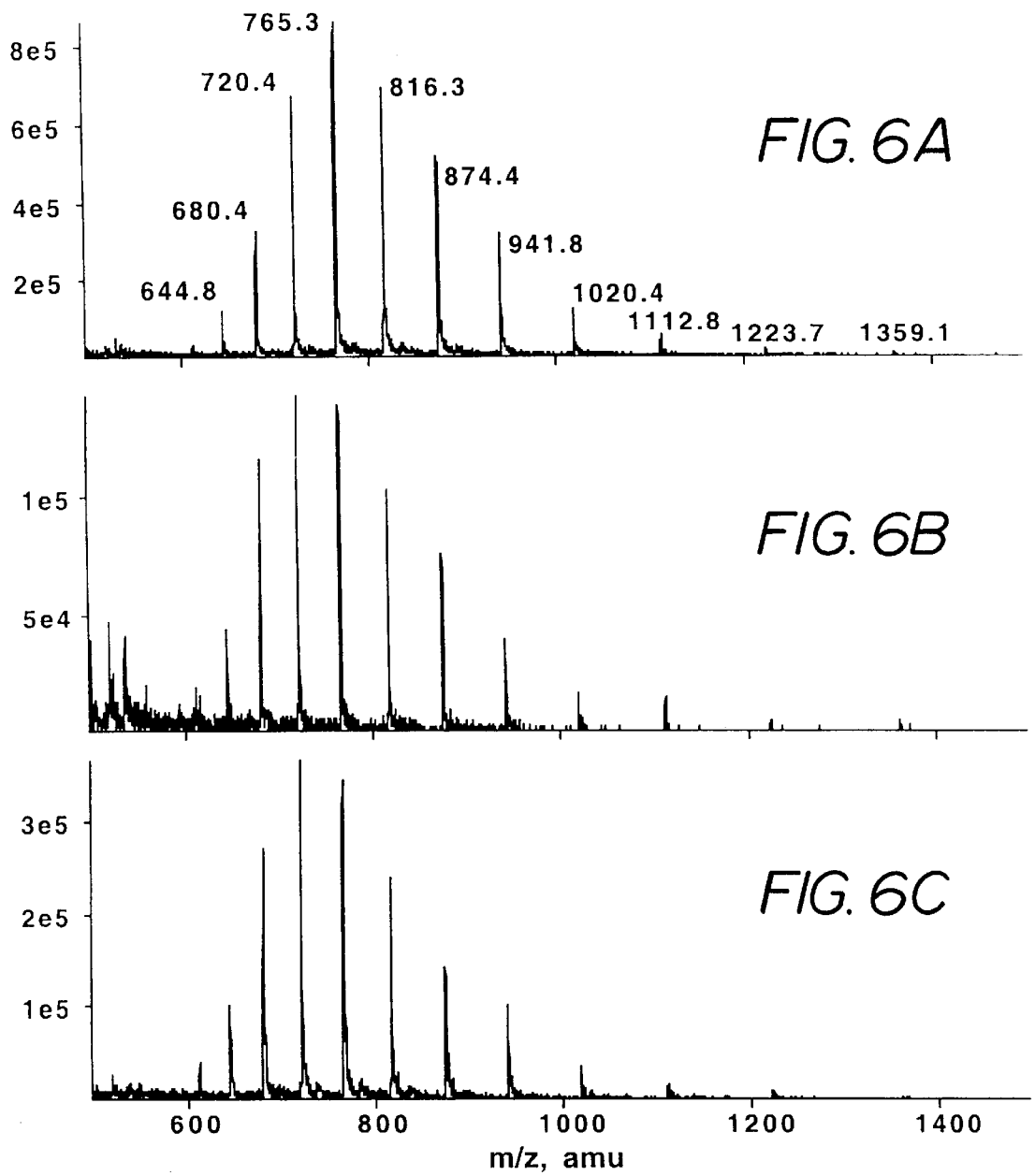

MINIATURIZED FLUID TRANSFER DEVICE

This application claims the benefit of U.S. Provisional Application No. 60/163,264, filed Nov. 3, 1999, the disclosure of which is hereby incorporated herein by reference.

FIELD OF THE INVENTION

The present invention relates, in general, to fluid transfer apparatus, and more particularly to miniature, pneumatically assisted electrospray devices.

BACKGROUND OF THE INVENTION

Miniaturized fluid transfer devices offer exciting opportunities for a wide range of applications. For example, such devices are extremely useful in the field of analytical chemistry and for convenience will be described herein with respect to electrospray apparatus for use in mass spectrometry. However, it will be understood that such devices are not limited to this particular application.

Although the application of chip-based analytical devices for zone electrophoresis separation of analytes with conventional spectroscopic detectors was first demonstrated many years ago, on-going developments have demonstrated impressive applications for analytical devices involving capillary electrophoresis (CE) particularly when performed on a chip-based substrate. Some recent reports have demonstrated CE separations within time frames of seconds and even milliseconds. Each of these reports has employed various spectroscopic detectors and used direct detection of analytes on the chip.

Atmospheric pressure ionization (API) mass spectrometry (MS) techniques also provide an important, alternative detection system for chip-based devices. Consequently, efforts to couple this technology with chip-based sample handling systems has attracted considerable recent interest. Developments in miniaturized chip-based devices for analytical applications that have appeared over the past decade suggest these devices coupled to API MS systems could provide some useful analytical advances.

Attempts to couple mass spectrometry with a chip-based fluid channel have, to date, required that the latter deliver the analyte via an electrospray plume directed to the ion sampling orifice of an API mass spectrometer. A strategy for producing a microelectrospray plume from the chip has evolved from direct spraying from the flat edge of the chip to improved means of producing an electrospray plume. One of these was an integrated miniaturized pneumatic nebulizer coupled via a subatmospheric liquid junction electrospray interface, while another was a pulled glass capillary centered in a carefully drilled flat-bottomed hole centered with the exit of a microfabricated CE channel in a glass substrate. Additional reports have included a sleeve to support the sprayer capillary on the edge of the chip as well as disposable emitters for CE/MS. Other developments have included gluing a pulled capillary sprayer on the flat, larger surface of the chip aligned with the CE channel. An alternative approach that may be applicable to chip-based separations has also been reported which employs a microfabricated monolithic nozzle surrounded by an annular cavity on the surface of a silicon substrate. In this device the fluid is delivered from the backside of a silicon chip substrate using fluid flows of a few hundred nanoliters per minute via a through-chip channel which terminates in a nanoelectrospray nozzle.

The foregoing developments demonstrate the continuing need for improved fluid transfer devices for use not only in electrophoresis and other analytical applications, but in numerous other fluid transfer applications in both micro and macro scales.

SUMMARY OF THE INVENTION

In a preferred embodiment, the fluid transfer device of the present invention is a miniature, pneumatically-assisted electrospray source that uses the suction effects of electrospray and the Bernoulli effect to pull a solution into a sprayer tube. The solution is provided by a concentric supply tube around the sprayer tube, with the supply tube being sealed at a front, or sprayer, end and open at the other, or back, end and which is slightly shorter than the sprayer tube. Solution supplied through a small hole in the supply tube near the middle of the tube flows rearwardly and protrudes out the back end of the supply tube, where it is sucked into the sprayer tube. The solution then is electrosprayed from the front end with pneumatic assistance. The solution has some surface tension where it protrudes from the back of the sprayer tube and this protrusion forms a free-standing liquid junction which can be used to make contact with a liquid or other material which may, for example, be within a separation channel in a glass, plastic or other based separation device. The resulting liquid junction at the back of the sprayer tube is thus free standing, its existence, size and form being dependent upon the flow rate, the viscosity, and the surface tension of the solution, the diameters of the various tubes used and their composition, the voltage on and the nature of the sprayer, and the characteristics of the pneumatic nebulizing portion of the sprayer.

In one application of the invention, the liquid junction of the device may be used to effectively couple a miniaturized condensed phase separation system; e.g., chip-based capillary electrophoresis (CE), capillary electrochromatography (CEC), or nano scale high performance liquid chromatography (HPLC), to the miniaturized spraying device without interfering with the separation device. Flow rates and voltages are selected such that the rate of solution fed to the liquid junction via an external pump just matches the rate of removal of the solution by the sprayer. By using a properly sized decoupling resistor between the metal sprayer tube to ground, condensed phase separations such as capillary electrophoresis (CE), capillary electro chromatography (CEC), or nano scale high performance liquid chromatography (HPLC) can be performed while maintaining independent spraying and separation conditions.

There are many other potential applications for the fluid transfer device of this invention, such as a direct coupling via the liquid junction to the surface of a thin layer chromatography (TLC) plate or to a single or two dimensional SDS PAGE plate for the direct analysis of chemical entities contained on the plate. Such additional applications could be of considerable use in forensic drug analysis applications or the proteomics field where important chemicals of interest may be characterized by electrospray-mass spectrometry.

BRIEF DESCRIPTION OF THE DRAWINGS

The foregoing, and additional objects, features and advantages of the invention will be apparent to those of skill in the art from the following detailed description of preferred embodiments thereof, taken in conjunction with the accompanying drawings, in which:

FIG. 1A is an enlarged view of the fluid transfer region of the device of FIG. 1;

FIGS. 6A, 6B and 6C are graphical illustrations of the summed spectra of cytochrome-c with make-up liquid 0.1% HCOOH in 80:20 MeOH:Water, showing in FIG. 6A 10 picomoles in solution of 1:1 MeOH:$H_2O$ 0.1% HCOOH; in FIG. 6B 10 picomoles in solution of water 0.1% HCOOH; and in FIG. 6C 20 picomoles deposited in a well and then reconstituted with sprayer and make-up liquid.

DESCRIPTION OF PREFERRED EMBODIMENTS

Figure 1:
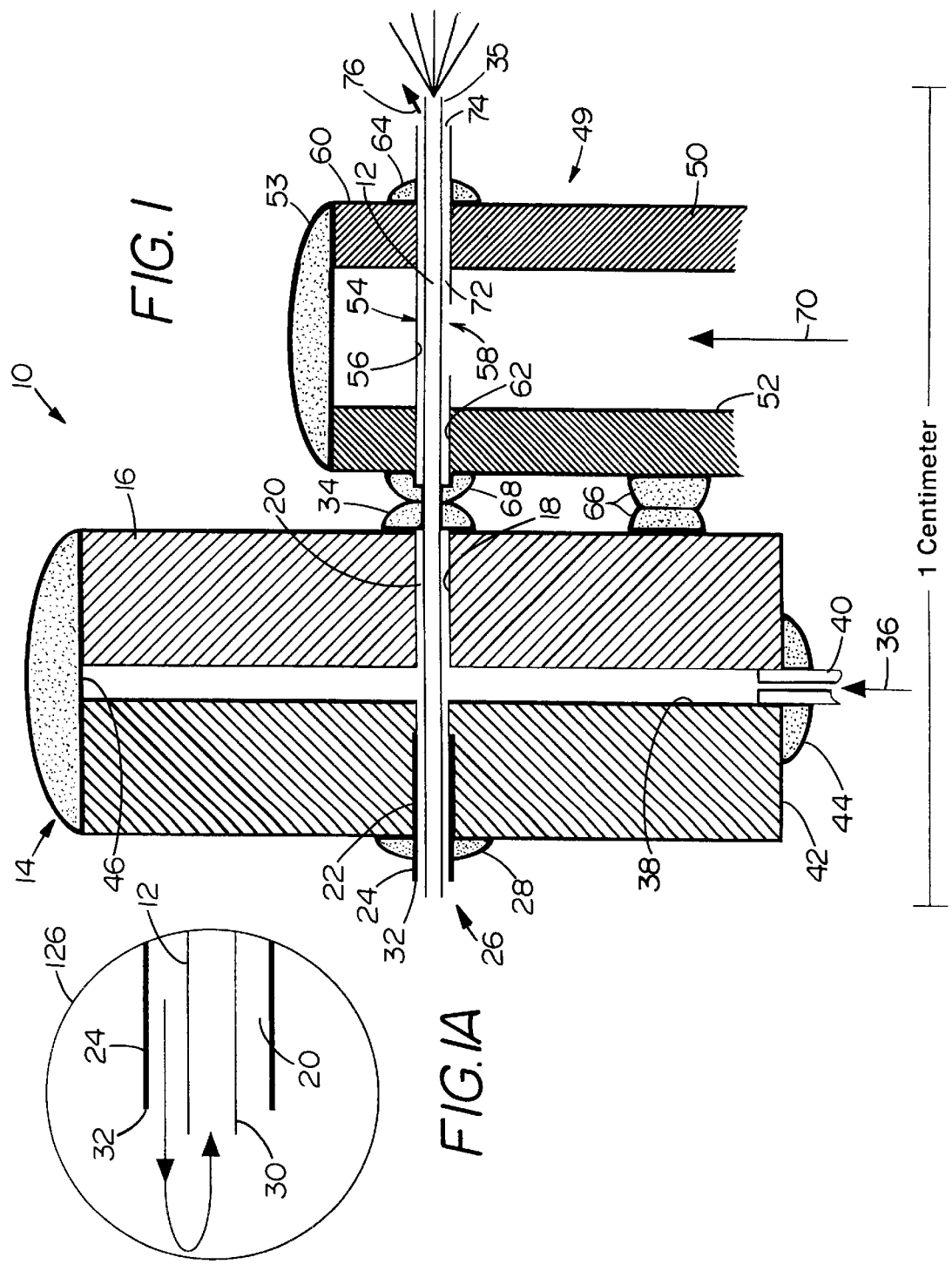
FIG. 1 illustrates a first embodiment of a fluid transfer device incorporating a self-contained liquid junction, in accordance with the present invention.
Figure 2:
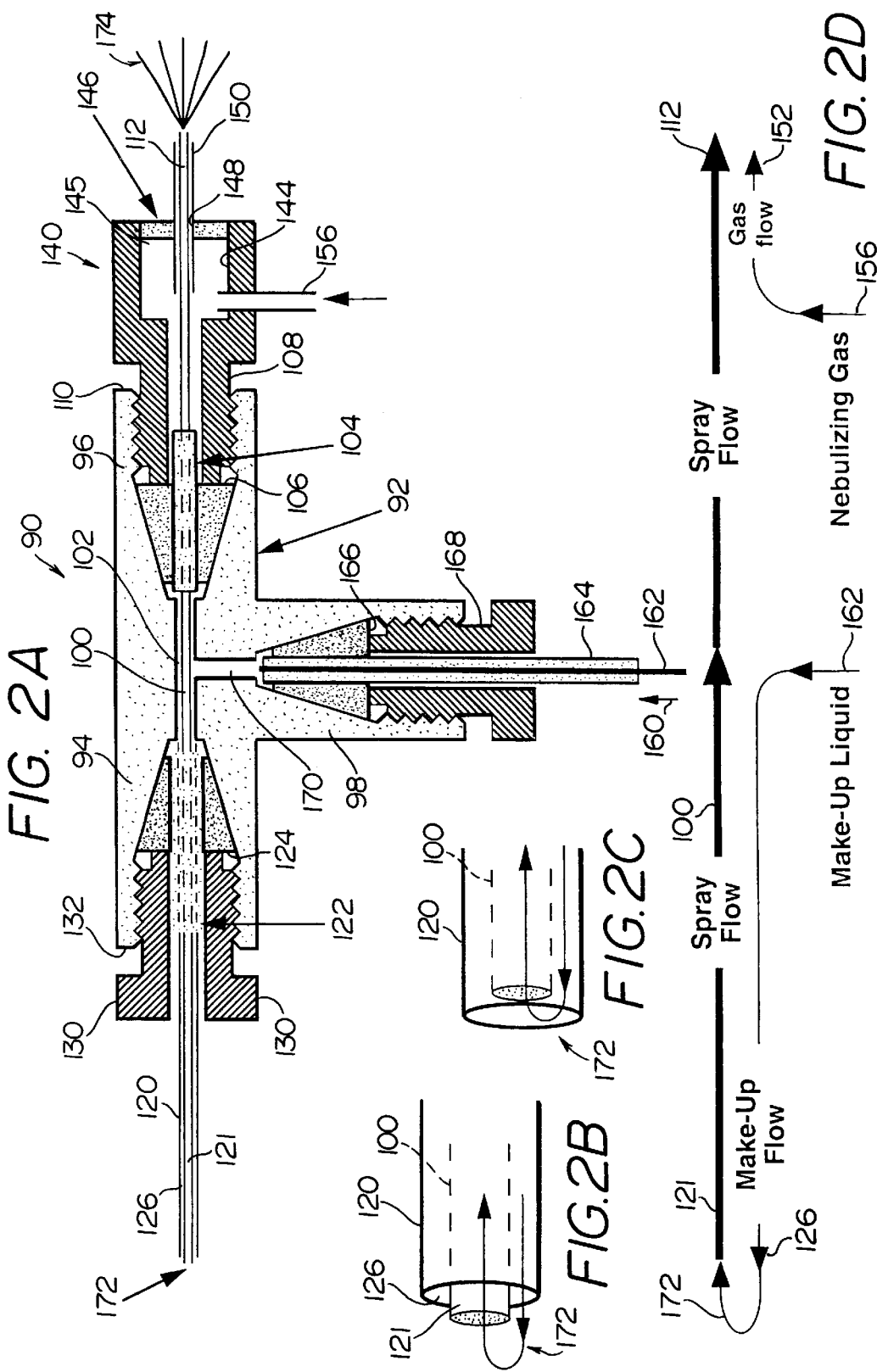
FIGS. 2A–2D illustrate a second embodiment of a fluid transfer device.

Turning now to a more detailed description of the invention, FIG. 1 illustrates a pneumatically assisted liquid transfer device 10 which, in this embodiment, is a low dead volume micro-sprayer system primarily intended for coupling to known chip-based separation systems (not shown). The device includes a metal sprayer tube 12 which preferably is a 1 cm length of 31 gauge stainless steel hypodermic tubing. A body portion 14 of the device is a make-up liquid supply tube 16 which, in this embodiment, is a length of 0.020 in. i.d.×0.0625 in. o.d. stainless steel tubing, with a small hole or aperture 18 drilled through the tubing in a direction perpendicular to the length of the tube 16 to receive the metal sprayer tube 12. The hole 18 is larger than the outer diameter of sprayer tube 12 to provide an annular channel 20 around the outside of spray tube 12, and is enlarged for part of its depth at 22 to receive a 0.3 cm length of 23 gauge stainless steel tube 24 which serves as a liquid delivery tube to a fluid transfer region 26, shown in the enlarged view of FIG. 1A. Tube 24 is held in place in hole 18 with a suitable adhesive, such as epoxy resin 28.

The metal sprayer tube 12 is inserted into the hole 18 in liquid make-up tube 16 so that an inlet end 30 of the sprayer tube 12 protrudes approximately 0.1–0.2 mm beyond the outlet end 32 of the liquid make-up tube 24 (see FIG. 1A). The sprayer tube 12 is held in place in hole 18 by epoxy 34, on the sidewall of the liquid supply tube 16. The outlet end 35 of sprayer tube 12 extends out of hole 18 in a direction opposite to the location of the inlet end 30. A make-up liquid, indicated by arrow 36, is supplied to a central passageway 38 in the supply tube 16 by way of a length of fused silica tubing 40 inserted into one end 42 of the tube 16 and sealed with epoxy 44. The other end 46 of the aperture 38 in the supply tube 16 is also sealed with epoxy 48.

A pneumatic nebulizer assembly 49 is incorporated in the device 10 by adding a gas supply line 50 having a central bore 52 closed at one end by epoxy 53, and a nebulizing tube 54 having a central bore 56. The gas supply line may be 0.0625 in. Teflon tubing, while the nebulizing tube 54 preferably is a 0.4 cm length of 23 gauge stainless steel tube in which the central bore 56 has an inner diameter larger than the outer diameter of sprayer tube 12. A small hole 58 is formed in the wall of tubing 54. The gas supply line 50 is pierced, for example near the closed end 60, by a transverse bore 62 which is perpendicular to the length of tube 50. The nebulizing tube 54 extends through the bore 62, with hole 58 located in the central bore 52 of supply line 50 so that bore 52 is in fluid communication with bore 56. Tube 54 is secured in bore 62 by epoxy 64. The nebulizing tube 54 fits over the outlet end 35 of sprayer tube 12, and the gas supply line 50 of the nebulizer assembly 49 is attached to the main supply tube 16 with epoxy resin, as at 66. Epoxy 68 also attaches assembly 46 to supply tube 16, and closes one end of tube 54.

A supply of nitrogen gas indicated by arrow 70 is controlled by a pressure regulator (not shown) to provide a nebulizing gas flow to the sprayer. The gas flows into bore 52, through hole 58 into bore 56, and flows through the annular space 72 between tubing 12 and tube 54, flowing out an annular opening 74 surrounding the outlet end 35 of tubing 12, as indicated by arrow 76. Electrical connection to the sprayer is via the metal supply tube 16.

In a test of the device of FIG. 1, the sprayer 10 was fastened with electrically insulating Teflon hardware to an xyz model K33-485 positioner (Edmund Scientific, Barrington, N.J.). During use, a stage was placed behind the xyz positioner to hold the sprayer so that the terminus of a capillary electrophoresis separation channel (not shown) could be aligned with the inlet end 30 of the sprayer, at which point liquid junction 26 could be formed. The combination sprayer and separation channel was then placed in front of an ion sampling orifice of a PE-Sciex API-III triple quadrupole mass spectrometer (Concord, Ontario, Canada). High voltage was supplied to the sprayer device 10 from a Bertan (Hicksville, N.Y.) Series 230, 5 kV high voltage supply. The high voltage supply was 'decoupled' from other voltages used on the separation channel chip for separation or injection by including a 25 megohm resistor from the sprayer supply to ground.

A second embodiment of the invention is illustrated in FIGS. 2A–2D, which show the construction of a related but larger minisprayer, generally indicated at 90, used, for example, in sampling solutions from multi-well plates, reconstituting and recovering samples in the wells of multi-well plates, or sampling materials on surfaces. The minisprayer 90 includes a body portion 92 which is a 1/16 in. stainless steel Tee having an inlet arm 94, an outlet arm 96, and a make-up arm 98, each equipped with requisite fittings and ferrules. A metal sprayer tube 100 is a length of 30 gauge stainless steel tubing projecting through a central passageway, or bore, 102 and is centered in bore 102 at the outlet arm 96 of the Tee with a short piece of 0.0625 in. o.d. PEEK tubing 104 of the appropriate inside diameter, a tapered PEEK ferrule 106 and a long-reach nut 108 threaded into the open end 110 of arm 96 to swage the ferrule 106 into a tapered bore in the arm. The tube 100 extends through the ferrule 106 and through a longitudinal passageway in nut 108 to provide an outlet sprayer end 112 for tube 100.

The sprayer tube 100 is centered in bore 102 at the inlet arm 94 of body 92 by a 1 cm length of 24 gauge stainless steel make-up liquid tube 120 which is slipped over the inlet end 121 of sprayer tubing 100 and held in the Tee with a short piece of 0.0625 in. o.d. Teflon tubing 122 and a PEEK ferrule 124. Tube 120 has an inner diameter which is larger than the outer diameter of tube 100 to provide an annular make-up liquid passageway 126 in fluid communication with bore 102. A nut 130 is threaded into the open end 132 of inlet arm 94 to swage ferrule 124 into a tapered bore in the arm and to secure the tubing 120.

To minimize the overall length of the sprayer 90, the nut 130 is shortened as much as possible while still retaining enough thread to allow tightening the ferrule 124. The 24-gauge make-up liquid tube 120 is positioned so that the sample inlet sprayer tube 100 protrudes approximately 0.1 mm when used for sampling from solid surfaces (see FIG. 2B). While sampling solutions, the make-up tube 120 is positioned so that the sprayer tube 100 is flush or slightly inside the make-up tube (see FIG. 2C).

In order to provide pneumatic nebulization and aspiration while maintaining a short path-length, a pneumatic nebulizer assembly 140 is provided for the sprayer device 90. The nebulizer assembly is incorporated into the same nut assembly that holds the sprayer tubing in the Tee. Thus, the head 142 of the long-reach nut 108 is drilled to an inside diameter 144 of ⅛ inch for approximately ¾ of the head length to provide a central chamber 145. A ⅛ inch diameter Teflon plug 146 equipped with a central hole 148 to accommodate a 24 gauge nebulizer tube 150 is press-fitted into the ⅛ inch drilled hole. The nebulizer tube 150 fits over the outlet end 112 of sprayer tube 100, leaving an annular nebulizing passage 152 surrounding outlet end 112. An inner end 154 of the tube 150 is in communication with chamber 145. The tube 150 can be moved along the length of the sprayer tube 100 to optimize the nebulization and aspiration process. A gas inlet tube 156 is epoxy-sealed into the side of the nut head 142 to communicate with chamber 145 and with passage 152.

A make-up liquid, indicated by arrow 160, is pumped through the arm 98 of the Tee 92 using appropriate fittings such as a liquid supply tube 162 extending through a support tube 164 and secured by a ferrule 166 and nut 168. The supply tube 162 is in communication with bore 102 via an inlet bore 170, and the infusion pump described above. Electrical contact is made to the metal Tee. To test its operation, the assembly 90 was mounted on an electrically insulating arm that could be rigidly positioned in front of a movable xyx stage. The stage and sprayer were positioned in front of the ion sampling orifice of a PE-Sciex API-IIIPlus mass spectrometer.

FIG. 2D illustrates the operation of the fluid transfer device 90. Nebulizing gas is supplied to inlet 156, and flows out of tube 150 through the annular outlet 152. This creates a suction at the outlet end 112 of tube 100, drawing fluid into the inlet end 121. This suction effect creates a fluid junction region 172 for aspiration of materials which are drawn along tube 100 and expelled at outlet end 112. A make-up liquid is introduced into the fluid junction 172 from inlet 162 through regions 170 and 102 and through tube 120, to ensure a fluid flow in the region that will assist in aspiration. The fluid expelled from outlet 112 is nebulized by the gas flow and the electrospray process at 152, as diagrammatically illustrated at 174 in FIG. 2A.

EXAMPLES

Figure 3:
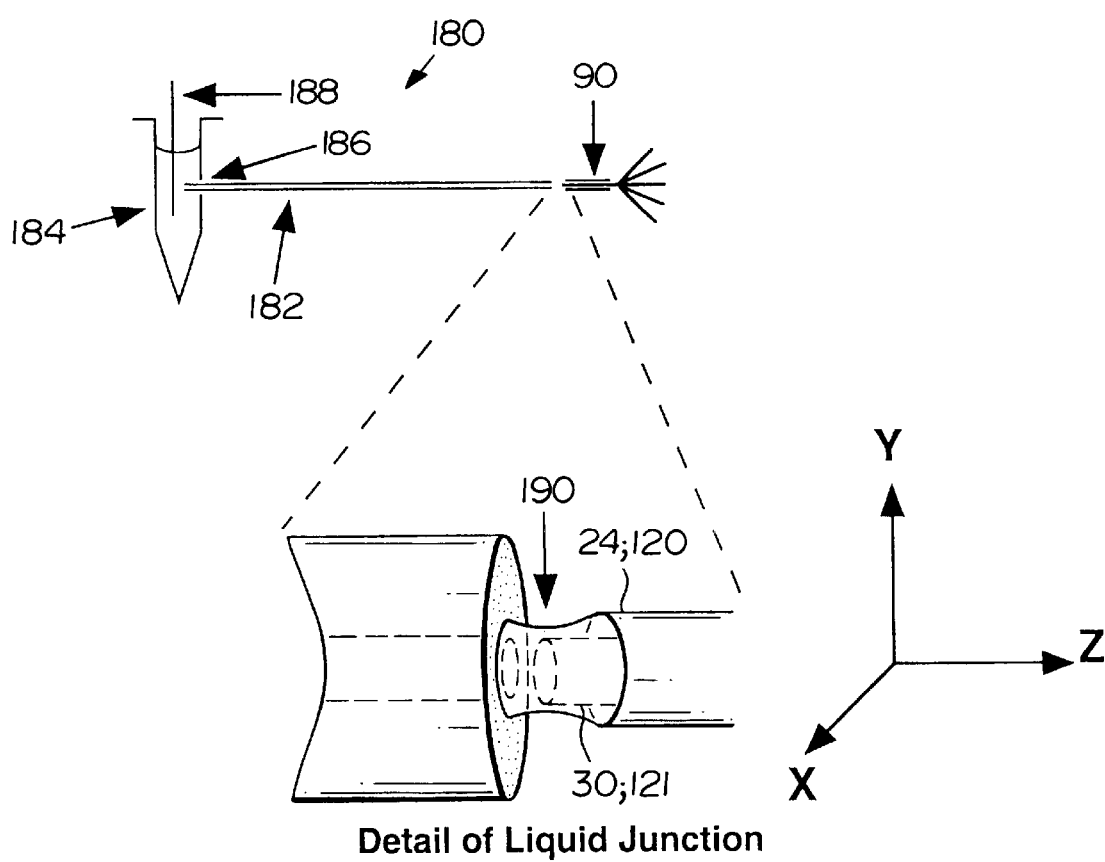
FIG. 3 is an enlarged view of a self-contained liquid junction produced by the embodiments of FIGS. 1 and 2.
Figure 4:
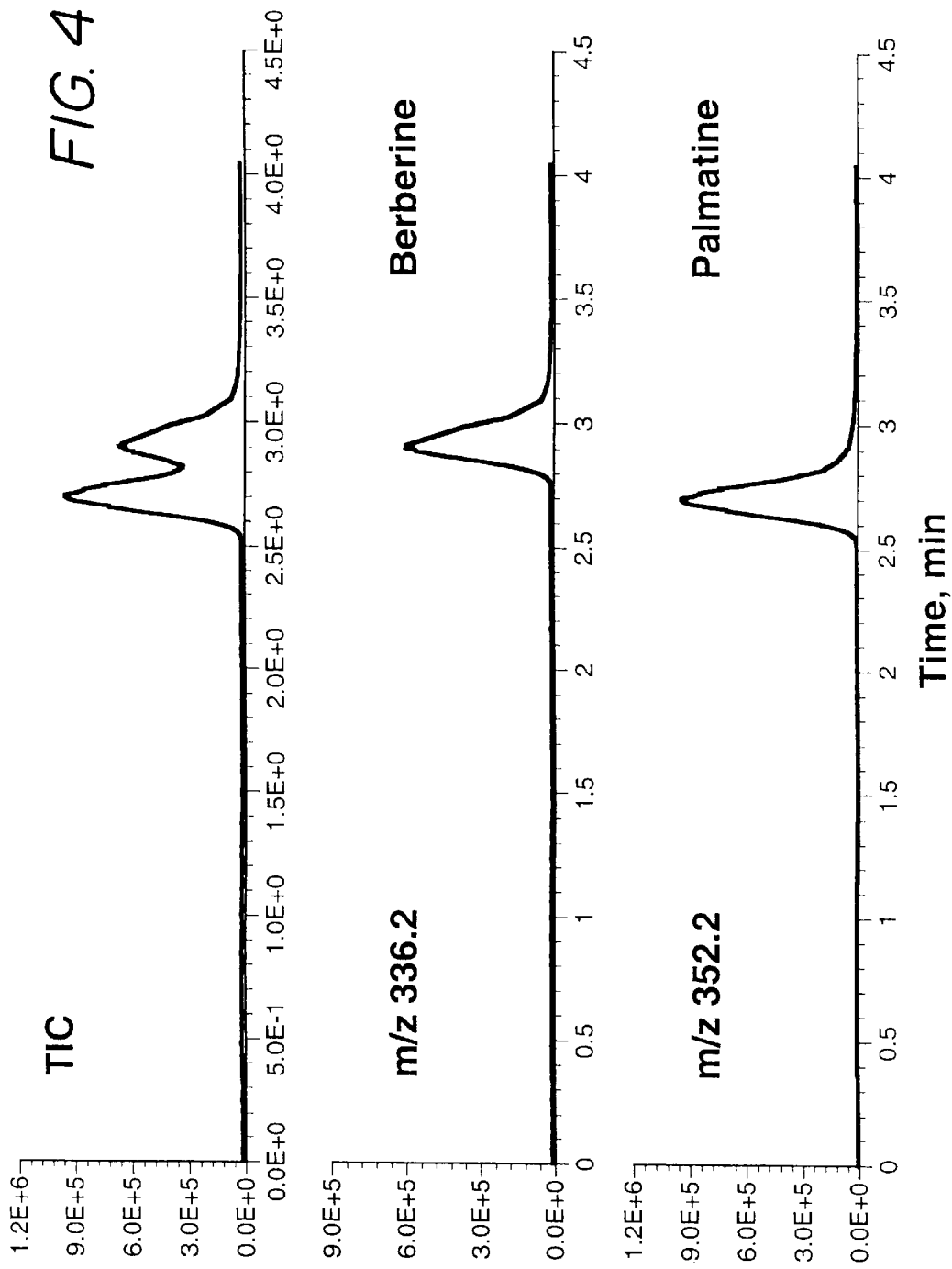
FIG. 4 is a graphical illustration of CE/MS with a "mock chip" (5 cm fused silica capillary) coupled via the liquid junction of FIG. 3.

A "mock" capillary electrophoresis (CE) chip 180, diagrammatically illustrated in FIG. 3, was constructed from a 6 cm length of 75 μm i.d.×375 μm o.d. fused silica tubing 182 attached to a glass microscope slide to demonstrate coupling the microsprayer of the invention to a chip-based separation device. Buffer and sample reservoirs were constructed from 1.5 mL polyethylene centrifuge tubes 184 that were held with a separate clamp. A hole 186 was drilled in the side of the centrifuge tube 184 below the liquid level and slightly larger in diameter than the fused silica tubing 182. The surface tension of the buffer was high enough to keep the buffer from leaking out of the hole in the reservoir. High voltage was applied for the CE separation via an electrode 188. A liquid transfer device 90 such as that illustrated in FIG. 1 was aligned with tube 182, and an ion spray voltage was applied to the sprayer as noted above and was decoupled from the CE voltage via a liquid junction 190 found between tube 182 and the sprayer 90, and the resistor to ground described above.

Multi-well plates used for sampling from wells with the above mini sprayer were either 384- or 1,536-well polystyrene plates (Greiner America, Lake Mary, Fla.). The 384-well plates were black while the 1,536-well plates were clear polystyrene. The clear plastic plates facilitated the positioning of the inlet of the sprayer during development stages. The plates containing samples of interest were mounted vertically on an xyz positioner to allow the inlet end of the mini sprayer (FIG. 2B) to reach into and near the bottom of a selected well. Observation of the sprayer position with respect to either a surface or a well was accomplished with a Watec (Las Vegas, Nev.) Model 502A CCD camera.

Reagents

Make-up liquid used for forming the liquid junction or for sampling from a multi-well plate was 80% methanol (Fisher Scientific, Pittsburgh, Pa.): 20% water prepared in-house with a Nanopure water system (Barnstead, Dubuque, Iowa). Depending upon the analyte chemistry, the bulk make-up liquid contained either 0.1% formic acid (GFS Chemicals, Columbus, Ohio) or 3 mM ammonium acetate (Fisher Scientific.) This solution was infused into the make-up tube at a rate of 2 to 6 μL/min depending upon the experiment. A 1 ng/μL solution of both berberine and palmatine (Sigma Chemical, St. Louis, Mo.) in water prepared by dilution from a 1000 ng/μL stock solution in methanol was used for the CE separation. A 2 ng/μL solution of berberine in methanol was prepared by dilution from a 1000 ng/μL stock solution in methanol. This solution was evaporated in a well to provide a dry residue to demonstrate the ability of the sprayer to recover a dried sample from a surface.

A stock solution of cytochrome-c was prepared by dissolving 1.5 mg of bovine heart cytochrome-c (Sigma Chemical) in 1:1 methanol:water 0.1% formic acid. This solution was then diluted to a concentration of 30 ng/μL (2 pM/μL) in 100% methanol, 0.1% formic acid or 15 ng/μL (1 pM/μL) in 1:1 methanol:water 0.1% formic acid or 100% methanol, 0.1% formic acid. For sampling a liquid from a multi-well plate 10 microliters of the 1:1 methanol solution or 100% aqueous solution was transferred to a well in a 1,536-well plate. For the reconstitution experiment, 10 microliters of the 100% methanolic solution of cytochrome-c was transferred to a well on a 1,536-well plate and the solvent allowed to evaporate leaving a dry residue of the sample on the surface of the well.

Procedure

For experiments requiring a low dead volume, such as coupling to a nano-separation chip, the microsprayer device of FIG. 1 was employed. For static experiments, such as sampling from wells, the larger minisprayer of FIG. 2 was used. The mass spectral data were collected in either the single MS full-scan mode or by selected ion monitoring (SIM). Unit mass resolution (peak widths of 0.5–0.7 Da at half-height) was maintained in all experiments. The sprayer voltage was maintained at 5 kV for all experiments reported here. Make-up flow and nebulizer gas flow rates were optimized for the specific experiment that was performed. The position of the sprayer tube relative to the make-up tube could be varied to optimize the performance of the larger minisprayer.

The microsprayer was used exclusively to couple a chip-based separation device to an API mass spectrometer via a free-standing liquid junction between the sprayer tube and the separation device. The free-standing liquid junction 190 detail shown in FIG. 3 is basically a dynamic, flowing 'liquid bridge' between the channel exit of the separation device and the inlet of the minisprayer. The bridge is maintained by the surface tension of the liquid, and is also affected by the distance between the inlet of the sprayer and the surface of the chip. Additionally, the make-up flow rate must balance the rate at which the liquid is being drawn into the sprayer by the combined effects of the electrospray process and pneumatic nebulization. The conditions for maintaining both a stable spray and a stable junction were determined empirically. The inlet of the sprayer was aligned with the separation channel of a 'mock chip' or other chip device, and make-up liquid flow initiated. High voltage was applied to the sprayer while nitrogen gas was introduced to the nebulizing tube. Once a spray was established, the voltage, gas pressure and make-up flow were adjusted for a stable spray while maintaining a narrow liquid bridge between the sprayer and the chip edge. Both high ion current signal intensity as well as low baseline noise were factors considered in the optimization process.

'Mock-Chip' CE/MS

A 6 cm length of 75 $\mu$m i.d. fused silica tubing 182 was used to simulate coupling of the sprayer to an actual chip (FIG. 3). The capillary 182 was filled with the optimized CE running buffer by sliding the capillary through the drilled hole 186 in the side of the centrifuge tube 184 and below the surface of the buffer which allowed capillary action to fill the capillary. The sprayer was then aligned with the fused silica tubing and positioned within approximately 50 micrometers of the end of the tubing. The position was monitored with a video camera in the x and z directions. The vertical position, y, was set by visual inspection. Sample loading was accomplished by interchanging the buffer reservoir with a sample reservoir. A metal electrode 188 in the solution provided the electrical contact for electrokinetic injection. The sprayer 90 coupled via the liquid junction 190 provides the counter electrode during electrokinetic injection. A difference of two thousand volts between the sample reservoir and the sprayer for 10 seconds provided a sufficient quantity of sample loaded into the inlet of the CE capillary by electrokinetic injection. After removing the applied voltage, the sample reservoir was interchanged with the buffer reservoir equipped with a metal electrode. Electrophoretic separation (FIG. 4) was achieved by supplying a higher voltage than the sprayer voltage to the electrode. An infusion experiment at 200 nL/min of a 1 ng/$\mu$L solution of reserpine in methanol was performed with PEEK tubing coupled with the sprayer to demonstrate the feasibility of employing the sprayer with substrates other than fused silica or glass.

Sampling from Surfaces and Solutions

Since the liquid junction is part of an open liquid system, the sprayer can be used to transfer analytes from surfaces or from sample solutions. The modifications of the sprayer shown in FIGS. 2B and 2C enable sampling from within the wells of multi-well plates and also from other surfaces where the dead-volume of the sprayer is of less concern, e.g. when not being used in conjunction with nanoscale separation devices. Three different modes of operation were used for this sprayer. The first mode involved sampling of an analyte from a surface by allowing a liquid junction to form between the sprayer inlet and the surface that held the analyte. This was demonstrated by evaporating to dryness 10 $\mu$L of a 2 ng/$\mu$L methanolic solution of berberine in a well of a 384-well plate and then inserting the sprayer into the well to form a liquid junction between the surface of the well and the sprayer (FIG. 5.) The ion current profile shown in FIG. 5 results from the reconstitution and uptake of the berberine dry residue. Thus the liquid junction formed between the inlet of the minisprayer (FIG. 2) and the dry residue of sample effectively redissolves or 'reconstitutes' the sample and transfers it through the minisprayer for ion spray mass spectrometric detection. FIG. 5 shows that the sample is introduced to the mass spectrometer within about 40 sec, increases to a maximum ion current signal in about one minute, and is consumed by the end of about two minutes. This process could be performed repeatedly if one required the sequential analysis of samples contained in their respective wells of these multi-well plates.

Full-scan ion spray mass spectrometric data are shown for two related solutions of cytochrome c contained in separate wells of a 1,536-well clear plastic plate (FIGS. 6A–B). The solution for FIG. 6A was 1:1 MeOH:water 0.1% HCOOH while that for FIG. 6B was 100% aqueous 0.1% HCOOH. In each case the make-up solvent was 0.1% HCOOH in 80:20 MeOH:water. This mode of operation employs the minisprayer to sample 1 pM/$\mu$L solutions of cytochrome-c contained in wells of a 1,536-well plate. By adjusting the make-up flow rate the sample solutions can be aspirated from the respective wells through the sprayer. When the analyte solution is significantly more aqueous than the make-up liquid, there will often be an initial dilution of the solution after which the solution will be picked up by the sprayer. Another mode involves reconstituting a dried sample of 20 picomoles of cytochrome-c from a well in a 1,536-well plate (FIG. 6C). In this mode the sprayer is inserted into the well and then nebulizing gas and sprayer voltage are turned off. The make-up flow is allowed to partially fill the well at which time the nebulizing gas and sprayer voltage are reapplied whereupon spraying commences. In either the solution sample mode or the reconstitution mode, the make-up liquid flow is adjusted to be slightly less than optimum for spray stability. This enables the sprayer to aspirate a portion of the bulk liquid while mixing it with the make-up liquid that is flowing into the sprayer. Additionally, the sprayer tube is kept just inside of the make-up tube rather than outside when a liquid junction formation is desired.

The selected ion monitoring mode (SIM)-CE/MS electropherogram shown in FIG. 4 demonstrates the viability of the sprayer system as an interface between a nanoscale separation system and an API-MS system. Although this experiment was performed on a 'mock chip' which consisted of a short length of fused silica capillary used to simulate an actual chip, the dimensions and conditions are similar to those experienced when using an actual chip-based device. This SIM-CE/MS determination of berberine and palmatine provided separation and detection of the respective quaternary cations of these compounds at m/z 336.2 and m/z 352.2 (FIG. 4.) The total selected ion current profile for the SIM CE/MS determination of these two analytical standards is shown in FIG. 4A. Although the two compounds are observed to be only partially separated in FIG. 4A, their respective electrophoretic profiles are clearly evident in FIG. 4B and FIG. 4C, respectively, where their corresponding selected ion current profiles at m/z 336.2 and m/z 352.2 are shown.

The symmetry of the electrophoretic peaks indicates low dead-volume conditions both within the sprayer and the liquid junction. The liquid junction is continuously renewed as the make-up liquid is swept from the outer make-up tube into the inner sprayer tube (FIG. 1). The sprayer tube has a calculated volume of approximately 125 nanoliters. At a flow rate of 4 $\mu$L/min for the make-up liquid the transit time through the sprayer tube would be approximately 1.9 seconds. The actual junction volume is on the order of 1–2 nanoliters; hence the transit time of a target analyte through the junction would be on the order of 20 milliseconds.

Figure 5:
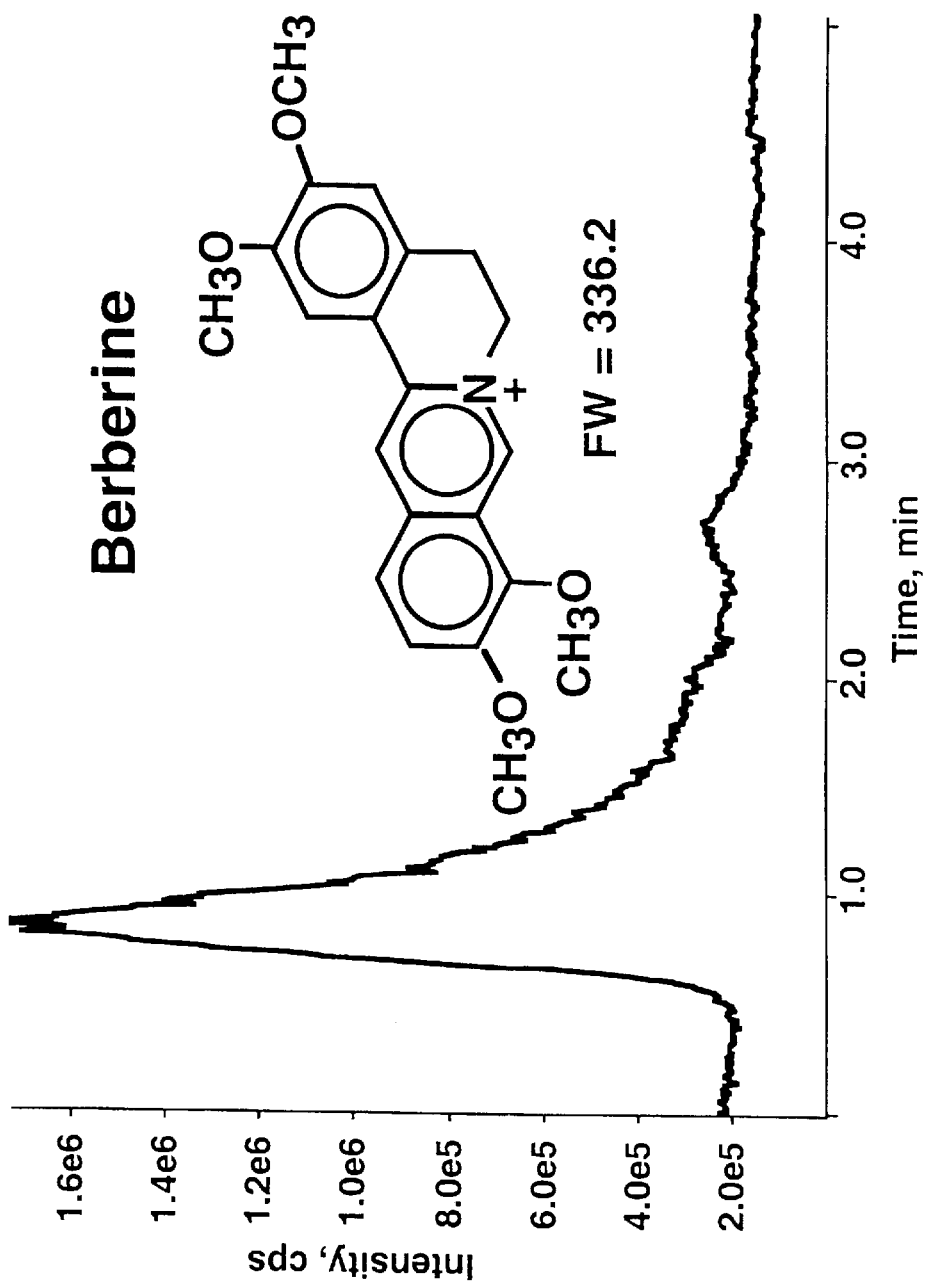
FIG. 5 is a graphical illustration of the sampling of twenty (20) nanograms of berberine from the bottom of a well on a 384 well plate with a SIM of m/z 336.2.

FIG. 5 shows the ion current profile for m/z 336.2 of berberine sampled from the bottom of a well on a 384-well plate. Ten microliters of a 2 ng/µL methanolic solution of berberine were placed in the well and allowed to evaporate. The plate was then mounted vertically on an xyz stage and positioned such that the sprayer pick-up capillary (FIG. 3) could reach into the well and form a liquid junction with the bottom of the well. As the sample of berberine was dissolved and drawn into the sprayer, the ion current increases until the sample is exhausted in that region of the well. This mode of operation could be quite useful for combinatorial chemistry studies, eliminating the need for dissolving and transferring samples from a well to a separate system for obtaining the mass spectrum. If the described system were to be operated in a robotic, automated mode it is possible that the high-throughput analysis of combinatorial library synthetic products could be possible. These analyses could provide rapid determination of product integrity as well as some information on the sample purity.

If the relative position of the make-up liquid tube is changed such that the sprayer inlet lies at the surface (flush) or withdrawn slightly inside the make-up liquid tube (FIG. 2C), the sprayer can readily combine the make-up liquid with a sample solution. If the make-up flow is adjusted such that it is less than the sprayer aspiration flow rate, then the sprayer can aspirate the surrounding sample solution in addition to the make-up liquid. This technique can be used to advantage when an aqueous sample solution is involved since aqueous solutions are often more difficult to electrospray. The rate at which the solution is actually sampled is not only a function of the make-up flow, but also the relative viscosities of the make-up liquid and the sample solution. If the viscosity of the sample solution is significantly higher than the make-up liquid it has been observed that there is actually a decrease in the spray flow with a resulting increase in solution volume until the composition of the liquid in the vicinity of the sprayer inlet becomes more similar to the make-up liquid.

FIGS. 6A,B show the electrospray mass spectra obtained from solutions of cytochrome-c contained in their respective wells of a 1,536-well plate. These summed spectra represent 10 picomoles of the protein in 1:1 methanol:aqueous 0.1% HCOOH (FIG. 6A), and also in 100% water containing 0.1% HCCOH (FIG. 6B). The ion current intensity for the protein dissolved in 100% aqueous solution is less than that in the 1:1 methanol:water 0.1% HCOOH solution as might be expected, but still a reasonable signal was obtained from what was originally a 100% aqueous system.

This same sprayer can be used in another mode to reconstitute dried samples (residues) such as peptides and proteins contained in wells. The make-up liquid is used first to redissolve or reconstitute the dry residue sample with the make-up whereupon the resultant solution is transferred to the sprayer for electrospray ionization. The sampling or inlet end of the sprayer (FIG. 2B) is inserted close to the bottom of a well while the sprayer is operating. Both the nebulizing gas and high voltage are then turned off while the make-up liquid flow continues. As the make-up liquid enters the well, material in the well may be dissolved or reconstituted. When the sprayer is again activated, the solution in the well is aspirated through the sprayer. The electrospray mass spectral data for 20 picomoles of cytochrome-c in the well are presented in FIG. 6C. Although there is the possibility for adsorptive losses of the protein to the walls of the well, an acceptable mass spectrum was obtained from the deposited 20 pmol of this protein. This method also reduces the potential losses associated with multiple transfers of 'sticky' samples. These three data sets of electrospray mass spectra for cytochrome-c reveal the same general behavior and demonstrate that the described mini-sprayer is capable of sampling a protein from either a solution or a dry residue contained in the wells of a 1,536-well plate. With automated transitional stages and proper control systems, an entire 1,536-well plate could be sampled robotically.

Although the invention has been described in terms of preferred embodiments, it will be understood that numerous modifications and variations will be apparent to those of skill in the art. Accordingly, the true spirit and scope of the invention are limited only by the following claims.

What is claimed is:

1. An aspirator/nebulizer-based fluid transfer system comprising:
   an elongated sprayer tube having an inlet end and an outlet end;
   a nebulizing tube at the outlet end of the sprayer tube for directing nebulizing gas having a flow rate past said outlet end;
   a make-up tube for supplying make-up fluid having a flow rate to a fluid transfer region adjacent said inlet end;
   a source of analyte provided at a spaced distance from the inlet end; and,
   means for adjusting the nebulizing gas flow rate and the make-up fluid flow rate to form a free-standing junction coupling the sprayer tube and the source of analyte,
   whereby said nebulizing gas causes aspiration of the make-up fluid and the analyte into and through said sprayer tube via the free-standing junction, and nebulizes fluid flowing out of said outlet end of said sprayer tube.

2. The aspirator/nebulizer of claim 1, wherein said make-up tube surrounds said inlet end of said sprayer tube.

3. The aspirator/nebulizer of claim 1, wherein said nebulizing tube surrounds said outlet end of said sprayer tube.

4. The aspirator/nebulizer of claim 3, wherein said make-up tube surrounds said inlet end of said sprayer tube.

5. The aspirator/nebulizer of claim 4, further including:
   a housing having a central bore which receives said sprayer tube and said make-up tube; and
   a make-up supply tube in said housing in communication with said make-up tube through said central bore.

6. The aspirator/nebulizer of claim 5, further including a nebulizer assembly in communication with said nebulizing tube for supplying a nebulizing gas to said nebulizing tube.

7. The aspirator/nebulizer of claim 6, wherein said nebulizer assembly includes a chamber for receiving nebulizing gas under pressure, said chamber being in fluid flow communication with said nebulizing tube.

8. The aspirator/nebulizer of claim 7, wherein said housing is a tee having aligned inlet and outlet arms incorporating said central bore receiving said sprayer tube and having a make-up arm intersecting said inlet and outlet arms, said make-up arm having a central passage intersecting said through bore and receiving said make-up supply tube.

9. The aspirator/nebulizer of claim 8, wherein said central bore in said inlet arm receives said make-up tube.

10. The aspirator/nebulizer of claim 9, further including ferrules swaged by threaded nuts in said inlet, outlet, and make-up arms of said tee for securing in said tee said make-up, nebulizer, and make-up supply tubes, respectively.

11. A pneumatically assisted fluid transfer system, comprising:

an elongated tube having an inlet end and an outlet end;

a source supplying analyte at a spaced distance from said inlet end;

a make-up fluid assembly at said inlet end for supplying make-up fluid having a flow rate to a fluid transfer region adjacent said inlet end of said elongated tube;

a gas supply assembly for directing gas having a flow rate toward said outlet end of said elongated tube to create suction at said inlet end; and, means for adjusting the make-up fluid flow rate, the gas flow rate and the spaced distance to form a free-standing junction coupling said inlet end and said source supplying analyte, through which the make-up fluid and the analyte are drawn through said elongated tube to be expelled from said outlet end.

12. The fluid transfer device of claim 11, wherein said make-up assembly includes a make-up tube having an axial bore for receiving make-up fluid and a transverse bore which extends across said make-up tube, intersects said axial bore, receives said elongated tube, and provides an annular fluid flow channel around said elongated tube.

13. The fluid transfer device of claim 12, further including a delivery tube secured in said transverse bore and surrounding said inlet end of said elongated tube, said delivery tube having a first end in fluid flow communication with said annular channel, and having a second end extending out of said make-up tube at said fluid transfer region.

14. The fluid transfer device of claim 13, wherein said inlet end of said elongated tube extends out of said second end of said delivery tube in said fluid transfer region.

15. The fluid transfer device of claim 14, said gas supply assembly including a gas supply tube having an axial bore for receiving gas under pressure and having a transverse bore which extends across said supply tube, intersects said supply tube axial bore, and receives said outlet end of said elongated tube.

16. The fluid transfer device of claim 15, said gas supply assembly further including:

a nebulizer tube in said gas supply tube transverse bore surrounding said outlet end of said elongated tube, the nebulizer tube providing an annular gas channel around said outlet end, and an aperture in said nebulizer tube providing gas flow communication from said axial bore of said gas supply tube to said annular gas channel to direct said gas toward said outlet of said elongated tube.

17. A fluid transfer device, comprising:

a sprayer tube having an inlet end and an outlet end;

an adjustable fluid flow apparatus producing suction at said inlet end;

a source supplying analyte at a spaced distance from said inlet end;

a liquid supply tube at said inlet end for supplying a make-up liquid to said inlet end;

means for adjusting the fluid flow, the make-up liquid flow and the spaced distance whereby the analyte and the make-up liquid are drawn into said inlet end by said suction via a free-standing liquid junction formed at said inlet end resulting from adjusting said fluid flow, make-up fluid flow and spaced distance.

18. A fluid transfer system, comprising:

an electrosprayer including, a sprayer tube having an inlet end and an outlet end, an adjustable applied voltage, a make-up fluid source having an adjustable flow rate at the inlet end, and a fluid flow apparatus having an adjustable flow rate at the outlet end for producing suction at the inlet end;

a source of analyte provided a spaced distance from the inlet end;

means for adjusting the gas flow rate, the make-up liquid flow rate, the applied voltage, and the spaced distance; and, a free-standing liquid junction formed to couple the electrosprayer and the source of analyte as the result of adjusting the gas flow rate, the make-up liquid flow rate, the applied voltage, and the spaced distance, whereby the make-up fluid and the analyte are drawn into the inlet end of the sprayer tube via the produced suction.

19. A method of forming a fluid transfer system, comprising the steps of:

providing an electrosprayer having an adjustable nebulizing gas flow rate, an adjustable applied voltage source, an inlet end and an outlet end;

providing a make-up fluid having an adjustable flow rate;

supplying a source of analyte at a spaced distance from the inlet end; and, adjusting the gas flow rate, the make-up liquid flow rate, the applied voltage, and the spaced distance to form a free-standing junction coupling the electrosprayer and the source of analyte, through which the make-up fluid and the analyte are drawn into the inlet end of the electrosprayer.

20. A fluid transfer system, comprising:

an electrosprayer having an adjustable nebulizing gas flow rate, an adjustable applied voltage, an inlet end and an outlet end;

a make-up fluid source having an adjustable flow rate;

a source of analyte provided at a spaced distance from the inlet end; and, means for adjusting the gas flow rate, the make-up liquid flow rate, the applied voltage, and the spaced distance to form a free-standing junction coupling the electrosprayer and the source of analyte, through which the make-up fluid and the analyte are drawn into the inlet end of the electrosprayer.

* * * * *